US008277397B2

(12) United States Patent
Ein-Gal

(10) Patent No.: US 8,277,397 B2
(45) Date of Patent: Oct. 2, 2012

(54) WAVE GENERATING DEVICE WITH INNER REFLECTOR

(76) Inventor: Moshe Ein-Gal, Ramat Hasharon (IL)

( * ) Notice: Subject to any disclaimer, the term of this patent is extended or adjusted under 35 U.S.C. 154(b) by 1734 days.

(21) Appl. No.: 11/152,194

(22) Filed: Jun. 15, 2005

(65) Prior Publication Data

US 2006/0287698 A1 Dec. 21, 2006

(51) Int. Cl.
*A61H 1/00* (2006.01)
*A61B 8/00* (2006.01)

(52) U.S. Cl. ................................ 601/2; 601/4; 600/439

(58) Field of Classification Search .................. 601/2, 4; 600/439; 367/140; 73/625, 627
See application file for complete search history.

(56) References Cited

U.S. PATENT DOCUMENTS 5,174,280 A * 12/1992 Gruenwald et al. .............. 601/4
5,793,001 A * 8/1998 Ferralli .......................... 181/155
7,167,415 B2 * 1/2007 Neeson et al. ................ 367/138
2003/0050559 A1 * 3/2003 Ein-Gal ........................ 600/437

FOREIGN PATENT DOCUMENTS

SU 978952 12/1982
WO 03/023760 3/2003

* cited by examiner

*Primary Examiner* — Long V. Le
*Assistant Examiner* — Katherine Fernandez
(74) *Attorney, Agent, or Firm* — Dekel Patent Ltd; David Klein

(57) ABSTRACT

A wave generating device including a reflective surface adapted to reflect energy waves to a focus, and an energy wave transducer positioned at least partially around and outwards from the reflective surface, and adapted to generate an energy wave inwards towards the reflective surface through a wave propagating medium disposed between the reflective surface and the energy wave transducer.

10 Claims, 1 Drawing Sheet

WAVE GENERATING DEVICE WITH INNER REFLECTOR

FIELD OF THE INVENTION

The present invention relates to generation and focusing of energy waves in general, e.g., acoustic waves, and particularly to a wave generating device, useful in medical treatments, such as but not limited to, extracorporeal shockwave treatment (ESWT), and other non-medical uses, such as but not limited to, non-destructive testing of structures, and particularly to a wave generating device wherein a reflector is placed inside a wave transducer.

BACKGROUND OF THE INVENTION

Generation and focusing of energy waves, such as acoustic waves (or shockwaves, the terms being used interchangeably throughout) for purposes of medical treatment such as lithotripsy (stone fragmentation) or orthopedic treatment are accomplished through a variety of methods. Each method incorporates acoustic wave generation and associated focusing apparatus.

The prior art may be classified according to the geometry of the acoustic wave generation and associated focusing:

a. Point source and ellipsoidal reflector: A point source typically comprises electrohydraulic apparatus. Fast discharges of electrical energy between tips of closely spaced electrodes give rise to a sequence of spherical waves in a propagation liquid. The electrodes are arranged with respect to an ellipsoidal reflector, which has two focal points. The electrical energy is discharged at the first focus, and the waves are focused onto the second focus.

b. Planar source and acoustic lens: A planar source typically comprises electromagnetic apparatus. A thin circular membrane applies pressure to the propagation liquid by being jolted or repelled away from a planar coil. Fast discharges of electrical energy into the coil and the associated rapid changes in the magnetic field induce currents in the membrane, turning it into a magnet with a polarization opposite to that of the coil. The ensuing repulsions of the membrane, which is in close contact with the propagation liquid, generate the acoustic waves. The waves are then focused by a lens to a target located at the focus of the lens.

c. Cylindrical source and parabolic reflector: The cylindrical source generates an acoustic wave that emanates radially outwards from the longitudinal periphery of the cylinder. For example, a coil may be mounted on a cylindrical support and a cylindrical membrane. The coil may be pushed or repelled radially, gives rise to outwardly propagating cylindrical waves. A parabolic reflector focuses the waves into a point on the cylindrical axis of the system. It is noted that the cylindrical source of the waves (also referred to as the cylindrical wave transducer) is inside the parabolic reflector.

d. Spherical source: Spherical waves may be generated by an array of piezoelectric transducers or by an electromagnetic approach with a spherical membrane being repulsed inwardly into the propagation liquid. No further focusing is required.

SUMMARY OF THE INVENTION

The present invention seeks to provide a novel wave generating device having a reflector placed inside a wave transducer, as is described more in detail hereinbelow. The wave generating device may have use in many medical applications, such as but not limited to, extracorporeal shockwave treatment (ESWT). The invention also has non-medical applications, such as but not limited to, non-destructive testing of structures.

There is thus provided in accordance with a preferred embodiment of the invention a wave generating device including a reflective surface adapted to reflect energy waves to a focus, and an energy wave transducer positioned at least partially around and outwards from the reflective surface, and adapted to generate an energy wave inwards towards the reflective surface through a wave propagating medium disposed between the reflective surface and the energy wave transducer.

In accordance with an embodiment of the invention the reflective surface and/or energy wave transducer may be formed by a shape revolved about an axis of revolution (e.g., parabolic, cylindrical, conical, etc.).

Further in accordance with an embodiment of the invention the energy wave transducer may include an electromagnetic element mounted on a support, the electromagnetic element being adapted to alternatively and repeatedly push and repel a repulsive member to produce inwardly propagating energy waves through the wave propagating medium.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
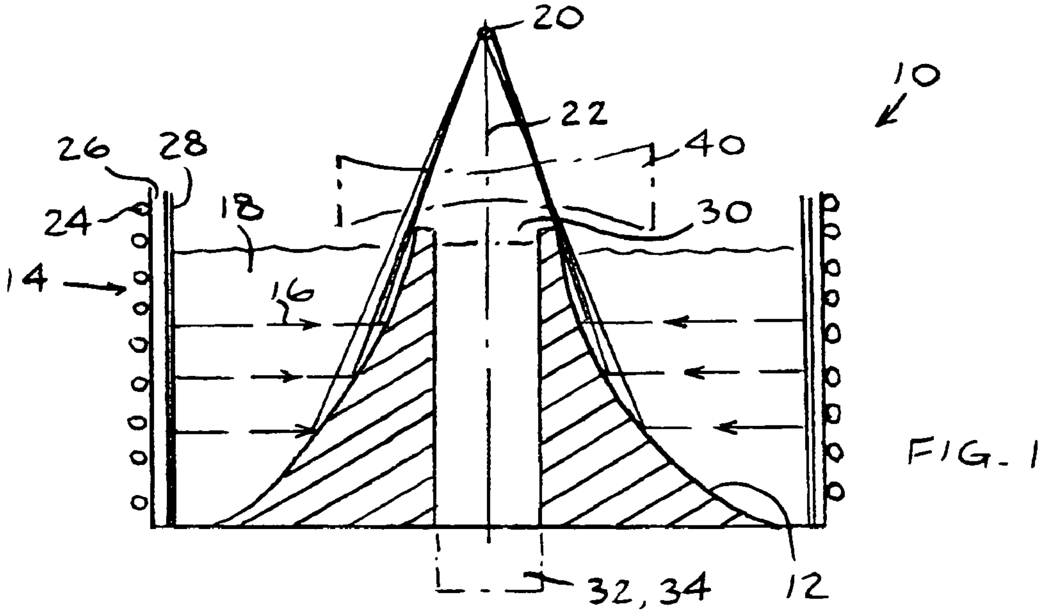
FIG. 1 is a simplified sectional illustration of a wave generating device, comprising a reflector placed inside a cylindrical wave transducer, constructed and operative in accordance with an embodiment of the invention.

Reference is now made to FIG. 1, which illustrates a wave generating device 10, constructed and operative in accordance with an embodiment of the invention.

The wave generating device 10 may include a reflective surface 12, which is reflective to energy waves, such as ultrasonic energy waves or electromagnetic energy waves. (For example, reflective surface 12 may be made of stainless steel or other suitable material.) An energy wave transducer 14 may be positioned at least partially around and outwards from reflective surface 12. The energy wave transducer 14 is capable of generating energy waves 16 inwards towards the reflective surface 12 through a wave propagating medium 18 (e.g., water) disposed between the reflective surface 12 and the energy wave transducer 14. The reflective surface 12 reflects the energy waves 16 to a focus 20 (in a target in a patient, for example).

Optionally, a beam shaping device 40, such as but not limited to, a concave focusing lens, may focus energy waves 16 to focus 20.

The reflective surface 12 may be formed by a shape revolved about an axis of revolution 22. The energy wave transducer 14 may also be formed by a shape revolved about the axis of revolution 22. For example, in the non-limiting embodiment of FIG. 1, the reflective surface 12 is parabolic and the energy wave transducer 14 is cylindrical. As is well known from the definition of a parabolic surface, any ray parallel to the axis of symmetry of the parabola (axis 22), which impinges upon the parabola, is reflected to focus 20.

Figure 2:
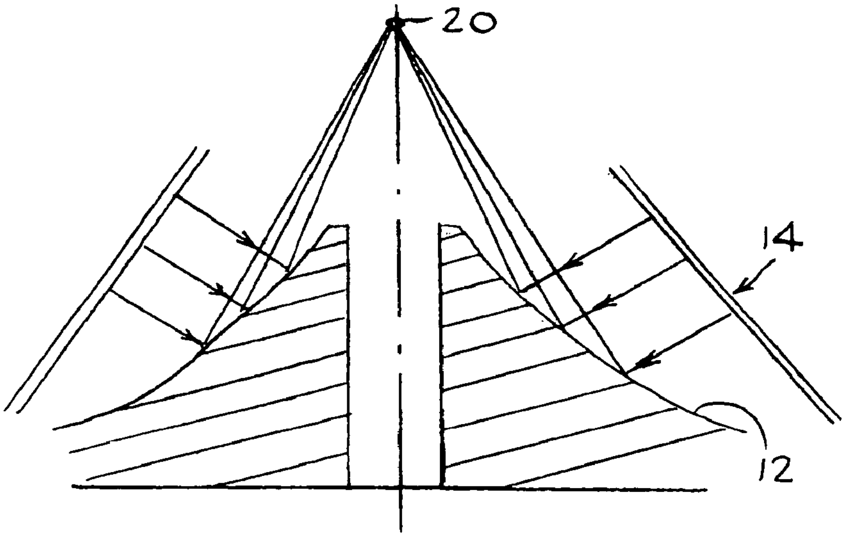
FIG. 2 is a simplified sectional illustration of a wave generating device, comprising a reflector placed inside a conical wave transducer, constructed and operative in accordance with another embodiment of the invention.

In the non-limiting embodiment of FIG. 2, the energy wave transducer is conical (straight surface tilted inwards towards the axis of revolution 22 and revolved about the axis of revolution 22) and the reflective surface 12 is parabolic (correspondingly tilted inwards towards the axis of revolution 22 so that the energy waves 16 are focused to focus 20. Other shapes (e.g., elliptical) may also be used to carry out the invention.

The energy wave transducer 14 may include an electromagnetic element 24 (e.g., a coil) mounted on a support 26. The electromagnetic element 24 alternatively and repeatedly pushes and repels a repulsive member 28 (e.g., a membrane) to produce inwardly propagating energy waves 16 through the wave propagating medium 18.

The reflective surface 12 may have an aperture 30 formed therein pointed towards the focus 20. A medical device, such as but not limited to, an imaging device 32 (e.g., X-ray probe, ultrasound probe, etc.) may be disposed in the aperture 30. Alternatively, an energy source 34 (e.g., X-ray source, etc.) may be disposed in the aperture 30.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. A wave generating device comprising:

a reflective surface adapted to directly reflect energy waves to a focus, said reflective surface being formed by a shape revolved about an axis of revolution, wherein said focus is located on said axis of revolution; and an energy wave transducer positioned at least partially around said reflective surface and radially outwards from the axis of revolution of said reflective surface, and adapted to generate an energy wave radially inwards towards said reflective surface through a wave propagating medium disposed between said reflective surface and said energy wave transducer.

2. The wave generating device according to claim 1, wherein said energy wave transducer is formed by a shape revolved about said axis of revolution.

3. The wave generating device according to claim 1, wherein said reflective surface is parabolic.

4. The wave generating device according to claim 1, wherein said energy wave transducer is cylindrical.

5. The wave generating device according to claim 1, wherein said energy wave transducer is conical.

6. The wave generating device according to claim 1, wherein said energy wave transducer comprises an electromagnetic element mounted on a support, said electromagnetic element adapted to alternatively and repeatedly push and repel a repulsive member to produce inwardly propagating energy waves through said wave propagating medium.

7. The wave generating device according to claim 1, wherein said reflective surface has an aperture formed therein pointed towards said focus.

8. The wave generating device according to claim 1, further comprising an imaging device disposed in said aperture.

9. The wave generating device according to claim 1, further comprising an energy source disposed in said aperture.

10. The wave generating device according to claim 1, wherein said energy wave transducer is positioned completely around said reflective surface.

* * * * *